(12) United States Patent
Rassibi

(10) Patent No.: US 10,390,916 B1
(45) Date of Patent: Aug. 27, 2019

(54) SALIVA EJECTOR APPLIANCE

(71) Applicant: Edmond Rassibi, West Hills, CA (US)

(72) Inventor: Edmond Rassibi, West Hills, CA (US)

(*) Notice: Subject to any disclaimer, the term of this patent is extended or adjusted under 35 U.S.C. 154(b) by 136 days.

(21) Appl. No.: 14/552,341

(22) Filed: Nov. 24, 2014

Related U.S. Application Data (60) Provisional application No. 61/915,821, filed on Dec. 13, 2013.

(51) Int. Cl.
*A61C 17/02* (2006.01)
*A61C 17/06* (2006.01)
*A61C 5/14* (2006.01)

(52) U.S. Cl.
CPC .............. *A61C 17/043* (2013.01); *A61C 5/14* (2013.01)

(58) Field of Classification Search
CPC .......................... A61C 17/043; A61C 17/0208
USPC ....................................................... 433/91–96
See application file for complete search history.

(56) References Cited

U.S. PATENT DOCUMENTS

| | | | | |
|---|---|---|---|---|
| 5,203,320 A | * | 4/1993 | Augustine | A61M 16/0488 128/200.26 |
| 5,720,275 A | * | 2/1998 | Patil | A61M 16/0488 128/200.24 |
| 6,309,218 B1 | * | 10/2001 | Ellenbecker | A61C 17/043 433/138 |
| 6,672,305 B2 | * | 1/2004 | Parker | A61M 16/0488 128/200.26 |
| 7,261,560 B2 | * | 8/2007 | Abo | A61C 17/043 433/91 |
| 8,012,141 B2 | * | 9/2011 | Wright | A61M 1/008 604/523 |
| 8,221,316 B2 | * | 7/2012 | DeGould | A61B 17/0206 600/205 |
| 8,852,169 B2 | * | 10/2014 | Milo | A61C 17/043 433/91 |
| 9,044,293 B2 | * | 6/2015 | Reyes | A61C 17/043 |
| 2003/0017433 A1 | * | 1/2003 | Reiz | A61C 17/043 433/93 |
| 2008/0166684 A1 | * | 7/2008 | Kanas | A61C 17/043 433/93 |
| 2010/0121152 A1 | * | 5/2010 | Boedeker | A61B 1/00094 600/187 |

* cited by examiner

*Primary Examiner* — Tammie K Marlen
(74) *Attorney, Agent, or Firm* — Pejman Yedidsion; Brooks Acordia IP Law, PC (57) ABSTRACT

A saliva injector appliance that includes an elongate member having a scoop with channels at its distal end. Clamps or the like hold the appliance against and to a saliva ejector such that the end of the injector is spaced a small distance rearward from the end of the scoop, and the scoop and the channels direct fluid into the injector and push tissue out of the way during a dental procedure. The elongate member has a rigid or semi-rigid construction and holds the saliva ejector at the desired position and angle as directed by a practitioner grasping the rear handle portion of the elongate member.

17 Claims, 6 Drawing Sheets

SALIVA EJECTOR APPLIANCE

CROSS-REFERENCE TO RELATED APPLICATIONS

This application claims priority to and the benefit of Provisional Patent Application No. 61/915,821 filed Dec. 13, 2013, the contents of which is hereby incorporated by reference herein in its entirety and for all purposes.

BACKGROUND

Saliva ejectors are used during dental procedures to suction liquids and other materials that might impede the procedures. They are usually made of a flexible plastic with an embedded metal wire that enables the device to retain a desired shape. Often the ejector will be fashioned in a specific shape in order to help push away tissue in the field for better visibility and protection from injury. The ejector may not be rigid enough to retain the desired shape for a substantial period of time, which can necessitate repositioning the ejector in the patient's mouth due to lack of suction or injury to the soft tissues surrounding the saliva ejector tip, or poor retraction of tissue. The procedure must then be interrupted to allow for the ejector to be fashioned again into the desired shape. This may happen multiple times during a procedure causing fatigue and stress on practitioners as well as the patients.

Often the saliva ejector is utilized only sporadically during dental procedures, such as during crown preparation. This is because the ejector is not rigid enough to retract the tissue, and so other tools, such as tongue retractors, must be used to accomplish the retraction. The ejector can then be used only when the practitioner puts the other tool down to free up one of his hands. The dental procedure is again interrupted, and saliva can pool in the patient's mouth making the patient uncomfortable.

SUMMARY

According to one aspect of the present disclosure provided herein is a device/appliance for attaching to a saliva ejector to stabilize it. A rigid ejector is thereby formed that effectively keeps soft tissue away from the dental procedure area and that can perform other actions to help keep the procedure area clear. An embodiment of the device/appliance affixes itself to the ejector by a groove and rigid projection to keep the ejector in the desired shape. Thereby the practitioner may manipulate the device in the patient's mouth and push away any tissue in the field for better visibility and protection of tissues.

According to another aspect, provided herein is a saliva ejector appliance for attaching to a saliva ejector so that the ejector can be used throughout the duration of most dental procedures by fulfilling the function of other devices (such as cheek retractors), namely retracting tissue thereby freeing up a practitioner's hand. The body of the saliva ejector appliance can take the form of multiple 'S' shaped curves facilitating a better view for the practitioner inside the patient's mouth thereby diminishing the amount of force needed to be applied by the practitioner, resulting in less hand fatigue.

According to yet another aspect, provided herein is a dental appliance for use in combination with a saliva ejector during a dental procedure to protect soft tissue in the patient's mouth by one or multiple protrusions of the appliance that extend past the suction tip of the saliva ejector.

According to a further aspect, provided herein is a dental appliance for use in combination with a saliva ejector to protect soft tissue in the patient's mouth, to stabilize the ejector, and to allow for the movement of the ejector in all areas of the patient's mouth. According to a still further aspect, provided herein is a dental appliance for use with a saliva ejector that improves the suctioning capabilities of the ejector by providing a channel for the saliva through one or multiple scoop-like protrusions at the tip of the appliance. These protrusions also extend the soft tissue in different directions away from the saliva ejector tip, which provides fluids greater access to the suction tip of the saliva ejector.

According to another aspect, provided herein is a device attachable to a saliva ejector and having one more protrusions at the head thereof to retract tissue during dental procedures.

Disclosed herein is a device/appliance for attachment to a saliva ejector for stabilizing the saliva ejector. The handheld device improves the functionality of the saliva ejector and in particular the suctioning capability of the ejector by providing a channel for the saliva through one or multiple scoop-like protrusions in the device that also protect the soft tissue from aspiration. The device advantageously can be maneuvered in all areas of the patient's mouth.

Further disclosed herein is a saliva ejector appliance, which includes an elongate member having a front face, a rearward portion and a forward end portion. The front face is structurally configured to hold a saliva ejector along generally an entire length of the front face with a distal end of the saliva ejector being spaced a small distance rearwardly from a distal end of the forward end portion.

Even further disclosed herein is a saliva ejector appliance that includes an elongate member having a front face, a rearward portion and a forward end portion, and at least one saliva ejector clamp. The forward end portion includes a scoop-like protrusion. The at least one saliva ejector clamp can be structurally configured to hold a saliva ejector along generally an entire length of the front face with a distal end of the saliva ejector being spaced a small distance rearwardly from an end of the forward end portion and thereby in a held position such that the scoop-like protrusion directs fluids to efficiently flow to the distal suction end of the saliva ejector.

Still further disclosed herein is a saliva ejector assembly having a saliva ejector and a head portion that extends out beyond the suction inlet of the saliva ejector tube. The head portion has channels to direct fluids to the inlet during a dental procedure, and the channels can be positioned in (or between) scoop-like protrusions that not only help direct the fluids to the inlet but also help to gently move tissue out of the way during the procedure. The assembly can further include a rigid handle, and the head portion can be the head portion of the handle. The handle can be a separate component from the ejector tube component of the assembly, or the handle and tube can be an integral construction.

Also disclosed herein is a method of carrying out a dental procedure including attaching a dental appliance to a saliva ejector such that a head portion of the appliance extends a small distance out from the suction tip of the saliva ejector. The head portion has at least one protrusion and at least one fluid channel. With the dental appliance attached, an aft handle portion of the dental appliance is grasped and the head portion manipulated in a patient's mouth during a dental procedure. The manipulating can include moving tissue out of the way of the suction tip with the at least one protrusion and sucking fluids from the patient's mouth into the suction tip using the at least one fluid channel.

Additionally disclosed herein is a head member that attaches to the end of the ejector tube such as by clip, clamp or screw means, or is permanently affixed thereto. The head member can include one or more channels, one or more projections and a scoop-like shape. Thereby, it gently pushes tissue out of the way during a dental procedure and directs fluids into the tip of the ejector tube.

Further objects, features and advantages of the disclosure will become apparent from a consideration of the drawings and ensuing description.

BRIEF DESCRIPTION OF DRAWINGS

Embodiments may be illustrated by way of example and not limitation in the figures of the accompanying drawings, and in which.

DETAILED DESCRIPTION

Figure 1:
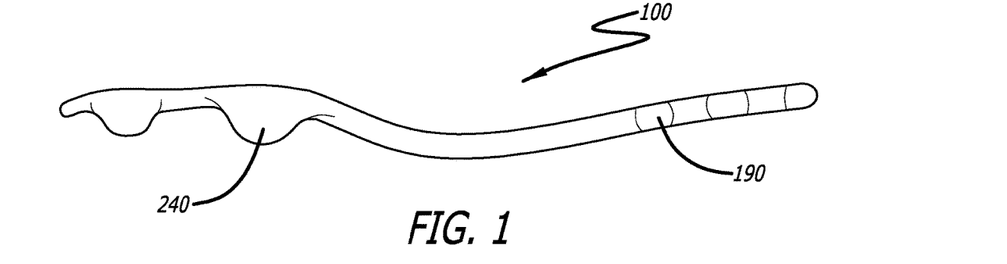
FIG. 1 is a left side elevational view of a stabilizer appliance of the present disclosure.
Figure 2:
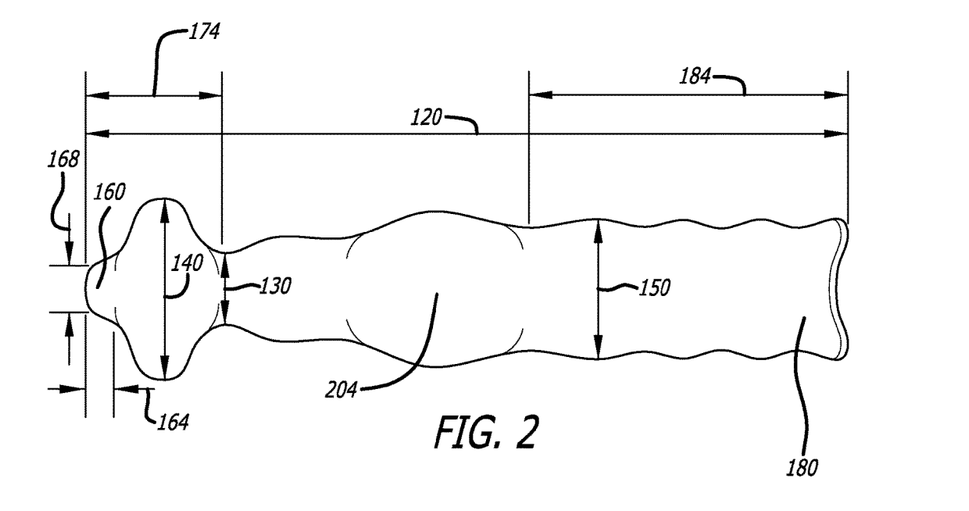
FIG. 2 is a top plan view.
Figure 3:
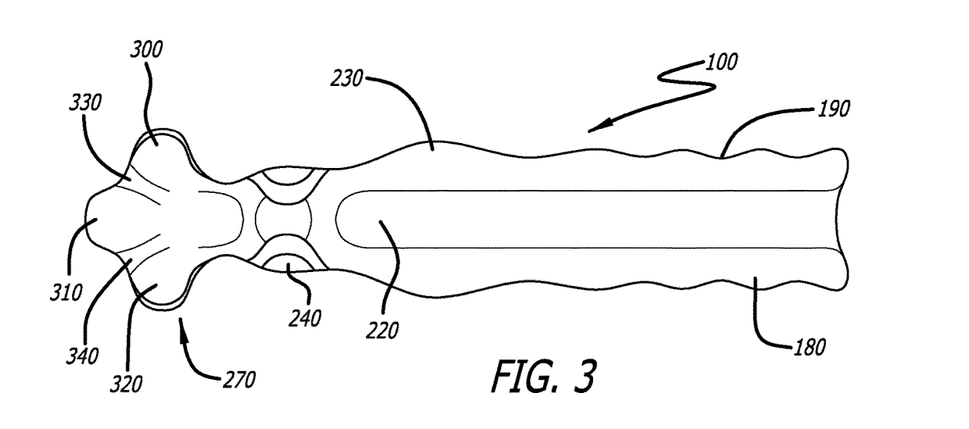
FIG. 3 is a bottom plan view.
Figure 6:
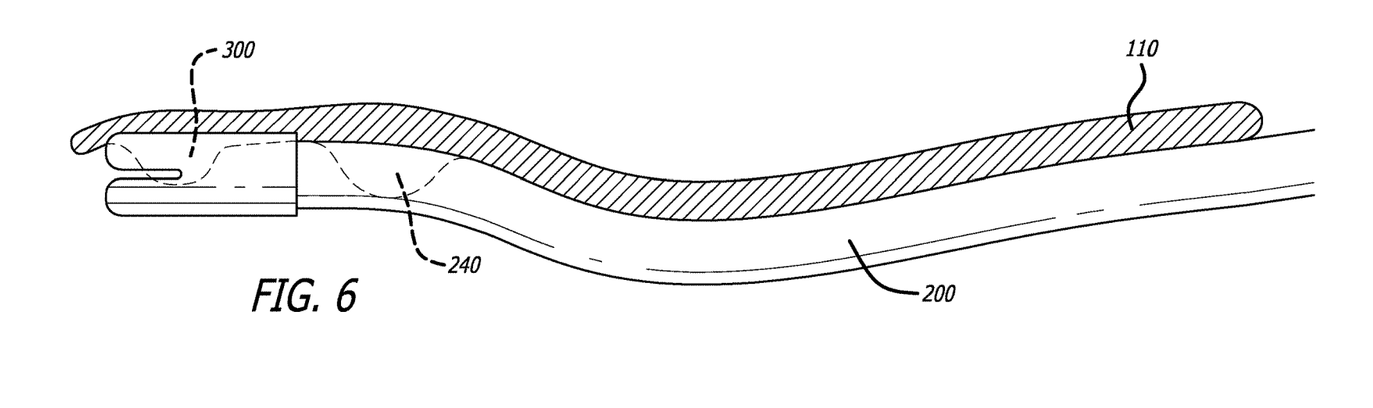
FIG. 6 is a cross-sectional view taken on line 6-6 of FIG. 5.
Figure 7:
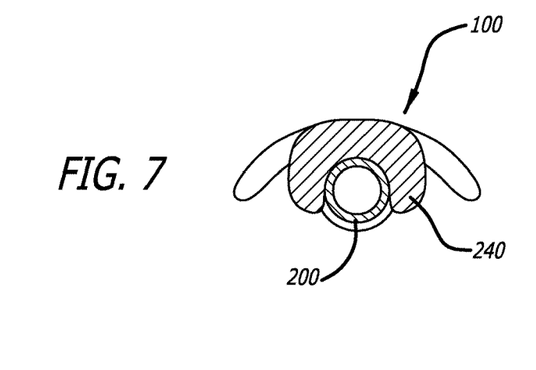
FIG. 7 is a cross-sectional view taken on line 7-7 of FIG. 5.
Figure 8:
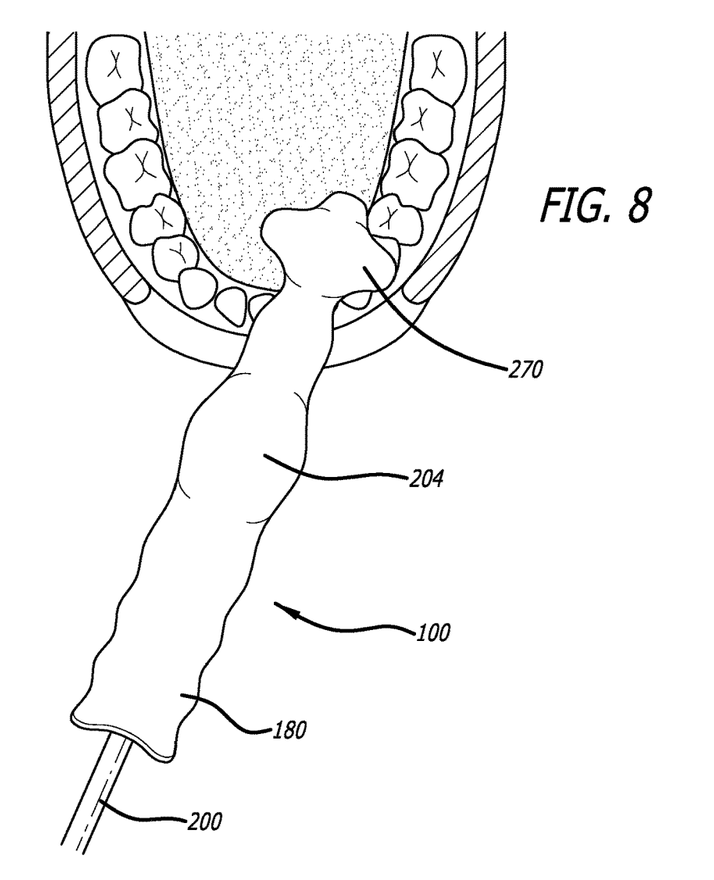
FIG. 8 is a top view of the stabilizer appliance and saliva ejector combination in an operative position in a patient's mouth.
Figure 9:
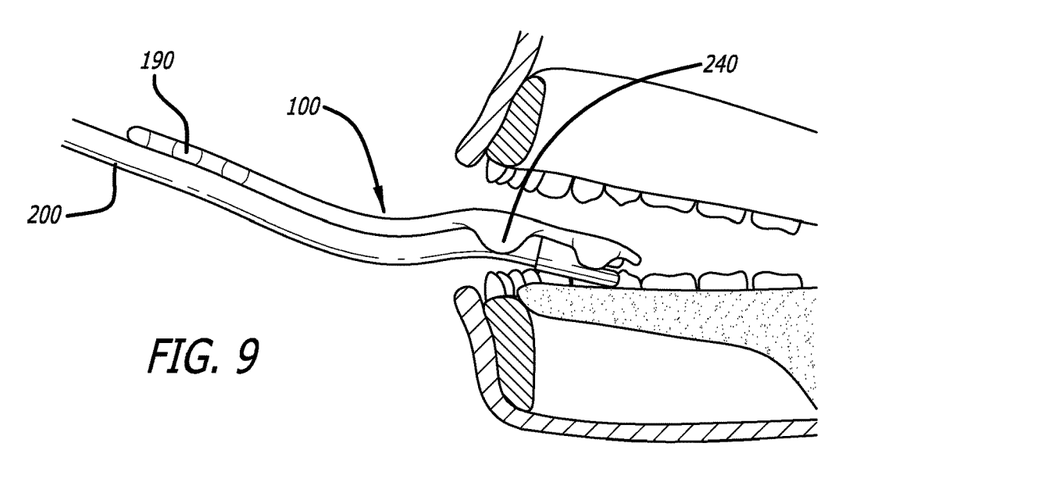
FIG. 9 is a side elevational view of the combination in an operative position and in a mouth of a dental patient.

A saliva ejector appliance of the disclosure is illustrated generally at 100 in isolation in FIGS. 1, 2 and 3. It may include an elongate member shown generally at 110 (FIG. 6) and having the following exemplary dimensions: a length 120 of approximately 100 (or between 100 and 180 mm); a width 130 (as viewed in FIGS. 2 and 3) of approximately less than seventeen mm at the throat; a width 140 of approximately seventeen mm at the head; and a width 150 of approximately between fifteen and twenty mm at the handle portion and the central portion. The tip 160 can have a length 164 of approximately five mm and a width 168 of approximately ten mm. The head can have a length 174 of approximately ten mm. The handle portion 180 can have a length 184 of approximately forty-five mm.

Figures 4, 5:
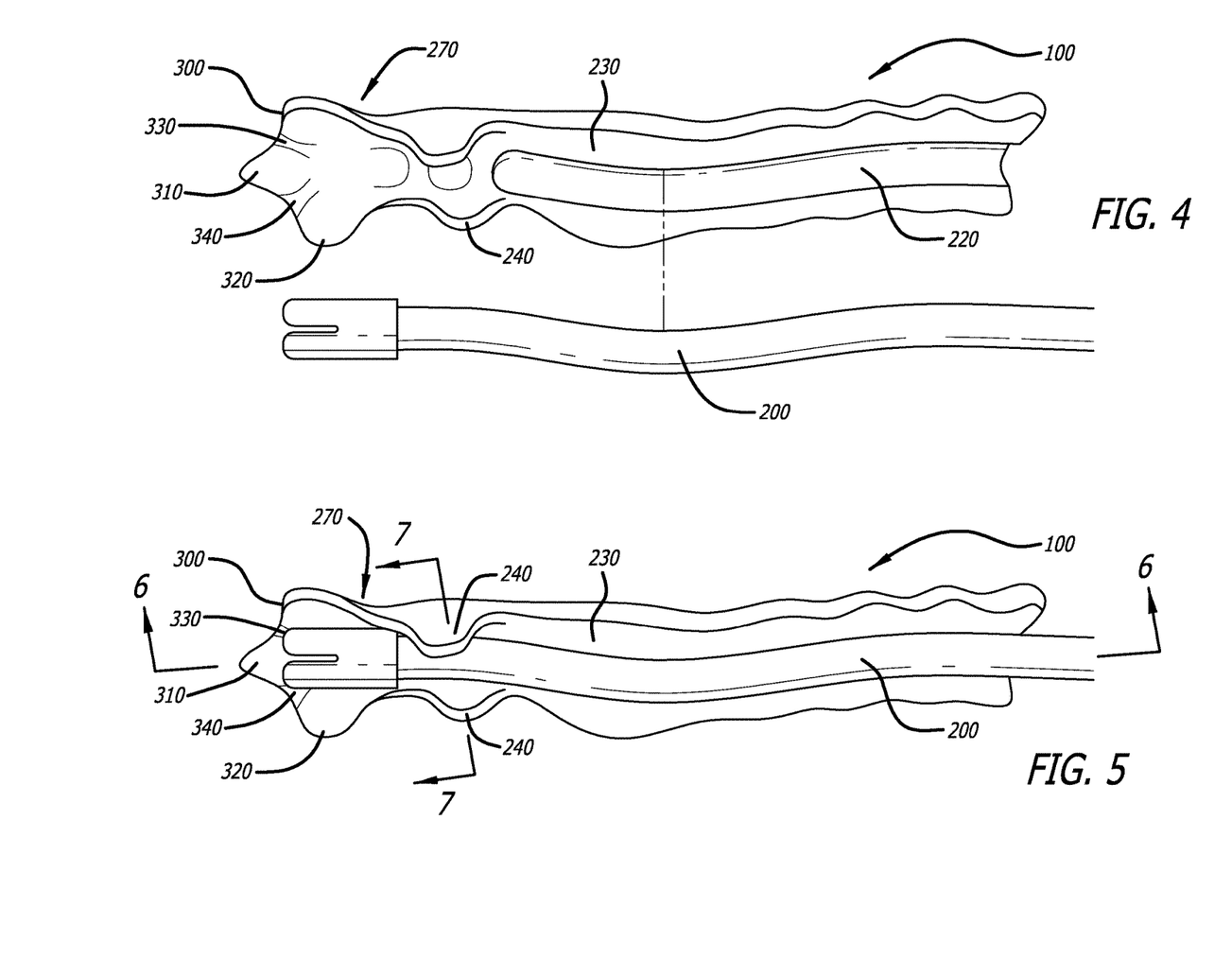
FIG. 4 is a bottom perspective view of the stabilizer appliance showing a saliva ejector being inserted into it.
FIG. 5 is a view similar to that of FIG. 4 showing the stabilizer appliance in place on the saliva ejector.

The handle portion 180 may have finger grooves or grips 190, and the elongate member 110 (FIG. 6) may have a thumb recess or rest 204 on the back side to help a practitioner grasp and maneuver the appliance 100 (and thereby the saliva ejector 200—FIG. 4) during a dental procedure. The handle grips 190 and thumb rest 204 by providing a comfortable ergonomic grip for the practitioner increase the accuracy of manipulation of the ejector 200 and also decrease the stress on the practitioner's hand or arm.

The elongate member 110 (FIG. 6) can be configured to hold an end portion of a saliva ejector 200 to it (or the saliva ejector to be held to the end portion). The holding configuration or construction of the elongate member can include a longitudinal groove 220 on a front face 230 for receiving a saliva ejector tube therein. (The tube can be in fluid communication with a vacuum source as is known in the art.) The holding configuration or construction can further include one or more clamps 240, also on the front face 230. The clamp(s) 240 can be integrally formed with the body of the elongate member 110 (FIG. 6) or they can be separately formed and connected to it by the manufacturer or the user. Another embodiment would be for the holding means to be on the saliva ejector 200. A further embodiment is discussed below with respect to FIG. 10.

The elongate member 110 (FIG. 6) can be made of a rigid or semi-flexible material that maintains the shape of the ejector 200. This enables the ejector 200 to be efficiently used for retraction and protection of tissue during procedures. An exemplary material is a stiff plastic that can be autoclaved or is cheap enough to make the device disposable.

As illustrated in the drawings, the saliva ejector appliance 100 can include a handle, with an end through which the distal end of the saliva ejector 200 fits and attaches to a vacuum source. An example of a saliva ejector 200 which can be used is the "Saliva Ejectors—6" Length—White—6" Length" available from TIDI Products, LLC.

The clamp 240 thus can be used to (releasably) secure the appliance 100 to the ejector 200. The tip of the ejector can rest in a niche or depression on the front face of the elongate member 110 so that the tip is approximately five mm (or between five and eight mm) from the tip end of the head portion 270. (A less preferable alternative embodiment can have the tip at the end of the head portion.) Three or more protrusions 300, 310, 320 can extend past the ejector tip to help direct fluids to the tip of the ejector in channels or grooves 330, 340 formed in or between the protrusions.

When viewed in side elevation as can be understood from FIG. 1, the elongate member 110 (FIG. 6) can have a generally flat S shape with differently curving portions. This shape makes it easier for the practitioner to hold and maneuver the appliance 100. It also allows for less pressure to be applied to the device to retract soft tissue, which means less hand fatigue for the practitioner.

Thus, the saliva ejector 200 is clamped by clamp 240 in the groove 220 that runs the length of the elongate member 110 (FIG. 6) of the saliva ejector appliance 100 and thereby keeps the saliva ejector stable throughout the dental procedures. The handle grooves 190 and thumb recess allow for decreased stress on the practitioner. Protrusions 300, 310, 320 extend past the ejector tip to prevent the aspiration of soft tissue, and also to extend the tissue beyond the saliva ejector tip in different directions to allow better visibility of the working area. The head portion 270 can be configured as a scoop to cause the surrounding tissue to conform to the appliance 100 and thereby allowing fluids easier flow into the tip of the saliva ejector 200. The scooped head portion 270 can have channels 330, 340 that guide the flow of saliva into the ejector 200. The entire unit is small enough to be easily and accurately maneuvered within the patient's mouth by a practitioner grasping the handle.

Figure 10:
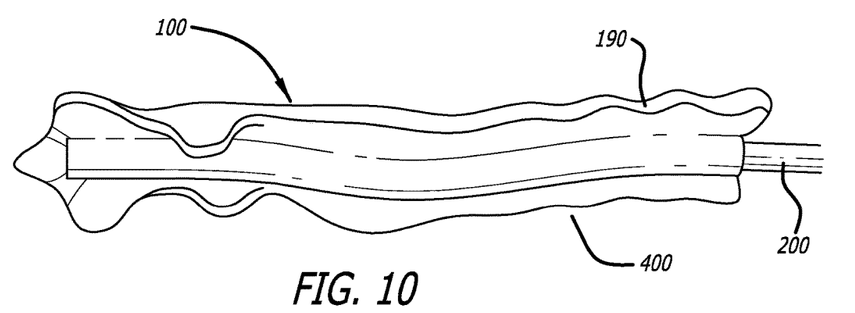
FIG. 10 is a bottom perspective view showing an alternative configuration wherein the stabilizer appliance and the ejector are constructed to be a single unit.

A further embodiment includes the appliance 100 and the ejector 200 being provided to the user as a single unit, such as shown in FIG. 10 generally at 400. It can be seen therein that the tube 200 extends through a passageway in the elongate member 110 (FIG. 6), and can be affixed therein.

Figure 11:
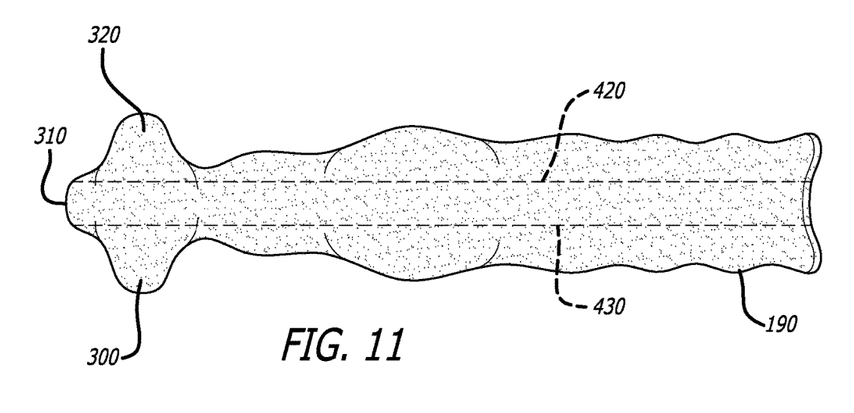
FIG. 11 is a top view of an alternative embodiment of the stabilizer appliance of FIG. 1, for example, wherein the appliance includes internal bendable wires.

The elongate member 110 (FIG. 6) can be a rigid, non-bendable member, or it can be bendable by the practitioner to the desired configuration. Additionally, to hold it in the desired configuration for the bendable embodiment, it can include one or more internal wires, as depicted at 420, 430 in FIG. 11.

Figure 12:
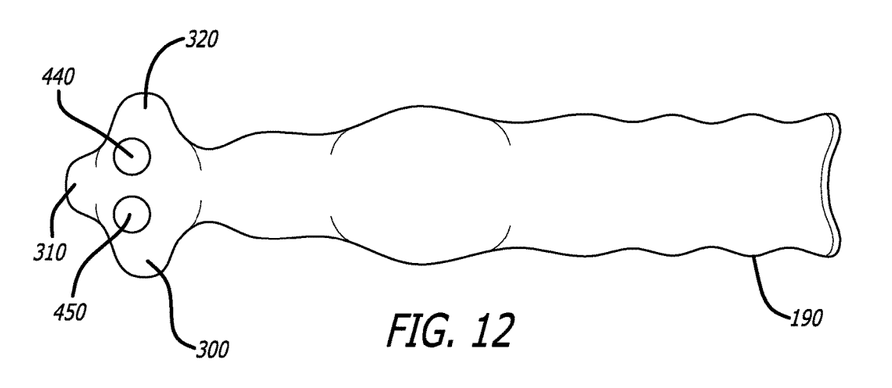
FIG. 12 is a top view of an alternative embodiment of the stabilizer appliance of FIG. 1, for example, wherein the head portion has holes allowing fluid transfer between the front and back of the appliance.

The head portion can include one or more front-back (top-bottom) through-holes 440, 450, as depicted in FIG. 12. These holes 440, 450 allow for fluid to pass through and reach the saliva ejector head.

Figure 13:
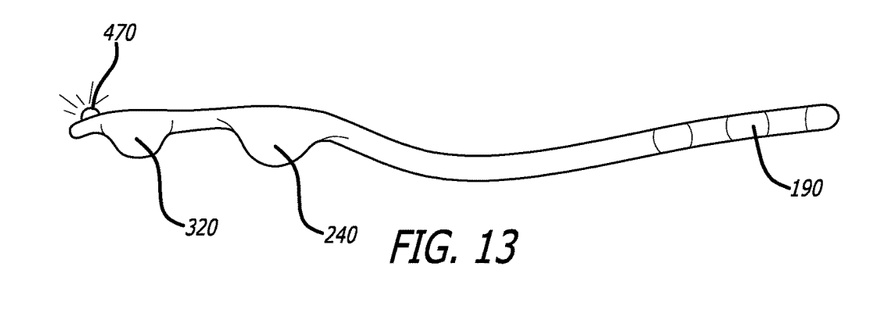
FIG. 13 is a side elevational view of an alternative embodiment of the stabilizer appliance of FIG. 1, for example, and which includes a light at the forward end.

An alternative construction includes a light 470 at a forward end portion of the elongate member 110 (FIG. 6), and as shown in FIG. 13. It can be disposed in an upward direction and is especially useful when additional illumination of the oral cavity is needed. The light 470 can be an LED type of light, powered by a battery. It helps the practitioner by illuminating the oral cavity for better visibility of the working area.

A further alternative is for the appliance to be a head member instead of the elongate member (that is, essentially the appliance without the handle portion). The head member appliance attaches to the end of the ejector tube, for example by clipping, clamping or screwing onto the end or by forming it as a combination therewith or integral part thereof. The head member can include one or more channels, one or more projections and a scoop-like shape, similar to the end portion of the above-discussed elongate member. It may be desirable to have a rod extending rearward from this head member and to which a length of the tube can be attached to give the tube some additional rigidity.

Exemplary embodiments of the saliva ejector appliance may comprise an elongate member having a front face, a rearward portion, and a forward end portion; and where the front face may be structurally configured to hold a saliva ejector along generally an entire length of the front face with a distal end of the saliva ejector being spaced a small distance rearwardly from an end of the forward end portion whereby the saliva ejector is in a held position. Additionally, the saliva ejector appliance may include a front face of the forward end portion where it has at least one channel structurally configured to direct fluid to the distal end when a saliva ejector is in the held position. Optionally, the at least one channel may comprise two channels in a fan shape. In one embodiment, the small distance may be approximately 5 mm. In another embodiment, the rearward portion may form a handle portion where the handle portion may comprise finger grips.

In another exemplary embodiment of the saliva ejector appliance, a back face of the elongate member comprises a thumb rest positioned for a thumb of a hand of a practitioner who is grasping the finger grips. Additionally, the elongate member may have a side elevational curved shape where the elongate member may have a central portion between the rearward portion and the forward end portion, and the curved shape comprises the elongate member curving in a front direction from the rearward portion towards the central portion and curving in a rearward direction from the central portion towards the forward end portion. Optionally, the curved shave may be a flattened S shape, the elongate member may be a rigid member, and the forward end portion may comprise a light where the light is disposed in a frontal direction, and may be a battery-powered LED light.

Other embodiments of the saliva ejector appliance may be in the form of a combination, the combination comprising: (1) a saliva ejector; and (2) a saliva ejector appliance comprising: (a) an elongate member having a front face, a rearward portion and a forward end portion; and (b) the saliva ejector being held along generally a substantial length of the elongate member with a distal end of the saliva ejector being spaced a small distance rearwardly from an end of the forward end portion. Further, the combination may be where a front face of the forward end portion has a scoop, and the scoop has at least one channel structurally configured to direct fluid to the distal end of the saliva ejector. In this embodiment, the elongate member has at least one clamp that releasably holds the saliva ejector to the front face.

In one embodiment, the forward end portion may comprise a plurality of scoop-like protrusions and the saliva ejector may pass through a through-passage of the elongate member and may be affixed in place therein. The combination may also have the elongate member comprise a practitioner handgrip at the rearward portion. In addition, the tube of the saliva ejector may extend through a passageway in the appliance and the elongate member may comprise a wire therein so that the member retains its shape when bent by a user to a desired shape. In some embodiments, the appliance may comprise a light and the elongate member may include a front-back through-hole in the forward end portion. Additionally, the saliva ejector may comprise a tube in fluid communication with a vacuum for exerting a vacuum force at the tip.

Method embodiments of conducting a dental procedure are also disclosed where the method may comprise the steps of (not necessarily in this order): (i) attaching a dental appliance to a saliva ejector such that a head portion of the appliance extends a small distance out from the suction tip of the saliva ejector; (ii) the head portion comprising at least one protrusion and at least one fluid channel; (iii) grasping an aft handle portion of the dental appliance and manipulating the head portion in a patient's mouth during a dental procedure; and (iv) the manipulating comprising moving tissue out of the way of the suction tip with the at least one protrusion and sucking fluids from the patient's mouth into the suction tip using the at least one fluid channel.

In one embodiment, the method may further comprise, before the manipulating, bending the appliance to a desired curvature. In one embodiment, the attaching may comprise clamping the dental appliance to the saliva ejector where the clamping may comprise using a clamp that is an integral part of the appliance or alternatively, the clamping may comprise the saliva ejector being in an elongate longitudinal groove of the dental appliance. The method may further be where the at least one protrusion may comprise a first protrusions, a second protrusions, and a third protrusions and the at least one channel may comprise a first channel between the first and second protrusions and a second channel between the second and third protrusions.

Individual elements or features of a particular aspect of the present teachings are generally not limited to that particular aspect, but, where applicable, are interchangeable and can be used in other aspects, even if not specifically shown or described. The same may also be varied in many ways. Such variations are not to be regarded as a departure from the present teachings, and all such modifications are intended to be included within the scope of the present teachings. For example, the clamps can be non-integral with the elongate member or holding means aside from clamps can be used. The present disclosure further includes sub-assemblies, as well as methods of using and/or making the appliance and/or components thereof and/or the combination of the appliance and the saliva ejector.

The terminology used herein is for the purpose of describing particular example embodiments only and is not intended to be limiting. As used herein, the singular forms "a," "an" and "the" may be intended to include the plural forms as well, unless the context clearly indicates otherwise. The terms "comprises," "comprising," "including" and "having" are inclusive and therefore specify the presence of stated features, steps, operations, elements and/or components, but do not preclude the presence or addition of one or more other features, steps, operations, elements, components and/or groups thereof. The method steps, processes and operations described herein are not to be construed as necessarily requiring their performance in the particular order discussed or illustrated, unless specifically identified as an order of performance. It is also to be understood that additional or alternative steps may be employed.

Although the terms first, second, third and so forth may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second" and other numerical terms when used herein do not imply a sequence or order unless clearly indicated by the context. Thus, a first element, component, region, layer or section discussed below can be termed a second element, component, region, layer or section without departing from the aspects of the present teachings.

When an element or layer is referred to as being "on," "engaged to," "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (such as "between" versus "directly between," and "adjacent" versus "directly adjacent"). As used herein, the term "and/or" includes any and all combinations of one or more of the associated listed items.

Spatially relative terms, such as "inner," "outer," "beneath," "below," "lower," "upper," "above," "forward," "rearward," "front," "back" "top" and "bottom" may be used herein for ease of description to describe one element's or feature's relationship to another, but the disclosure is intended to encompass different orientations of the appliance in use or operation in addition to the orientation depicted in the figures. For example, if the appliance in the figures is turned over, elements described as "below" or "beneath" other elements or features would then be oriented "above" the other elements or features. Thus, the example term "below" can encompass both an orientation of above and below. The device may be otherwise oriented (rotated ninety degrees or at other orientations) and the spatially relative descriptors used herein interpreted accordingly.

Although the present inventions have been described in terms of preferred and alternative embodiments above, numerous modifications and/or additions to the above-described embodiments would be readily apparent to one skilled in the art. The embodiments can be defined as methods of use or assembly carried out by anyone, any subset of or all of the components and/or users; as systems of one or more components in a certain structural and/or functional relationship; and/or as subassemblies or sub-methods. The inventions can include each of the individual components separately. However, it is intended that the scopes of the present inventions extend to all such modifications and/or additions and that the scopes of the present inventions are limited solely by the claims set forth here below.

What is claimed is:

1. A saliva ejector system comprising:
   a saliva ejector configured to:
      suction materials from a patient's oral cavity, and
   a saliva ejector appliance comprising:
      an elongate member having a front face, a rearward portion, and a forward head portion;
      the front face having a longitudinal groove configured to hold therein in a snap-fit held position and affixed in place, the saliva ejector along generally an entire length of the front face with a distal end of the saliva ejector being spaced a small distance rearwardly from an end of the forward head portion, wherein the forward head portion is continuous with the rearward portion in a longitudinal direction;
      the rearward portion forming an operator handle portion of the appliance when the saliva ejector is in the held position allowing an operator grasping the handle portion to controllably move the forward head portion in the patient's oral cavity in a saliva ejection procedure; and
      the handle portion being longer than the head portion, and
   wherein the saliva ejector appliance is configured to:
      stop the saliva ejector at the oral cavity by holding in place the saliva ejector to the front face; and
      protect soft tissue in the patient's oral cavity by extending past a tip of the saliva ejector and thereby preventing the aspiration of soft tissue.

2. The saliva ejector system of claim 1 wherein the handle portion has finger grips on an outer side portion of a surface thereof.

3. The saliva ejector system of claim 1 wherein the forward head portion includes a scoop-shaped head that includes two channels in a fan shape and configured to direct fluids to the tip of the saliva ejector when in the held position and during a saliva ejection procedure and at least one projection configured to push tissue out of the way.

4. The saliva ejector system of claim 3 further configured to move tissue out of the way of the tip of the saliva ejector with the at least one protrusion and allow suction of fluids from the patient's oral cavity into the tip of the saliva ejector using the at least one fluid channel.

5. The saliva ejector system of claim 1 wherein the forward head portion includes a scoop-shaped head defining a pocket and having a forward end tip, and the pocket has a width greater than a width of the longitudinal groove.

6. The saliva ejector system of claim 1 wherein the handle portion is made of a semi-rigid material such that a user can manually bend the handle portion into a desired changed shape, and thereby configured to be maneuvered within the patient's oral cavity by a practitioner grasping the handle portion.

7. The saliva ejector system of claim 1 wherein the forward head portion has a scoop shape configured to direct fluid to the distal end when a saliva ejector is in the held position preventing the saliva ejector from further movement.

8. The saliva ejector system of claim 1 wherein the forward head portion has lateral downwardly-angling ears.

9. The saliva ejector system of claim 1 wherein the forward head portion comprises one or more through-holes to allow for fluid to pass through and reach the saliva ejector.

10. A saliva ejector system comprising:
a saliva ejector configured to suction materials from a patient's oral cavity, and
a saliva ejector appliance comprising:
an elongate member having a front face, a rearward portion, and a forward head portion;
the forward end portion including a scoop-shaped head defining a pocket and having a forward end tip; and
the front face having a longitudinal groove configured to hold therein in a held position and affixed in place, the saliva ejector along generally an entire length of the front face with a slotted soft tip of the saliva ejector being positioned in the pocket and a forward end of the soft tip being spaced a small distance rearwardly from the forward end tip; wherein the slotted soft tip has a larger diameter than a flexible tube portion of the saliva ejector, and wherein the forward head portion is continuous with the rearward portion in a longitudinal direction;
the pocket having a width greater than a width of the longitudinal groove;
the rearward portion forming an operator handle portion of the appliance when the saliva ejector is in the held position allowing an operator grasping the handle portion to controllably move the forward head portion in the patient's oral cavity in a saliva ejection procedure; and
the handle portion being longer than the head portion; and
wherein the saliva ejector appliance is configured to:
stop the saliva ejector at the oral cavity by holding in place the saliva ejector to the front face; and
protect soft tissue in the patient's oral cavity by extending past a tip of the saliva ejector and thereby preventing the aspiration of soft tissue.

11. The saliva ejector system of claim 10 wherein the handle portion is made of a semi-rigid material such that a user can manually bend the handle portion into a desired changed shape.

12. A saliva ejector appliance system comprising:
a saliva ejector configured to suction materials from a patient's oral cavity, and
a saliva ejector appliance comprising:
an elongate member having a front face, a rearward portion, and a forward head portion;
the front face having a longitudinal groove configured to hold therein in a held position and affixed in place, the saliva ejector along generally an entire length of the front face with a distal end of the saliva ejector being spaced a small distance rearwardly from an end of the forward head portion, wherein the forward head portion is continuous with the rearward portion in a longitudinal direction;
the rearward portion forming an operator handle portion of the appliance when the saliva ejector is in the held position allowing an operator grasping the handle portion to controllably move the forward head portion in the patient's oral cavity in a saliva ejection procedure; and
the handle portion being longer than the head portion;
the elongate member has a neck adjacent to and proximal to the head portion; and
the elongate member has an enlarged, operator thumb rest on a bottom surface adjacent to the neck; and
wherein the saliva ejector appliance is configured to:
stop the saliva ejector at the oral cavity by holding in place the saliva ejector to the front face; and
protect soft tissue in the patient's oral cavity by extending past a tip of the saliva ejector and thereby preventing the aspiration of soft tissue.

13. The saliva ejector system of claim 12 wherein the handle portion is made of a semi-rigid material such that a user can manually bend the handle portion into a desired changed shape.

14. A saliva ejector system comprising:
a saliva ejector configured to suction materials from a patient's oral cavity, and
a saliva ejector appliance comprising:
an elongate member having a front face, a rearward portion, and a forward head portion;
the front face having a longitudinal groove configured to hold therein in a held position and affixed in place, the saliva ejector along generally an entire length of the front face with a distal end of the saliva ejector being spaced a small distance rearwardly from an end of the forward head portion, wherein the forward head portion is continuous with the rearward portion in a longitudinal direction;
the rearward portion forming an operator handle portion of the appliance when the saliva ejector is in the held position allowing an operator grasping the handle portion to controllably move the forward head portion in the patient's oral cavity in a saliva ejection procedure;
the handle portion being longer than the head portion; and
the handle portion being made of a semi-rigid material such that a user can manually bend the handle portion into a desired changed shape; and
wherein the saliva ejector appliance is configured to:
stop the saliva ejector at the oral cavity by holding in place the saliva ejector to the front face; and
protect soft tissue in the patient's oral cavity by extending past a tip of the saliva ejector and thereby preventing the aspiration of soft tissue.

15. The saliva ejector system of claim 14 wherein the forward head portion includes a scoop-shaped head that includes two channels in a fan shape and configured to direct fluids to the tip of the saliva ejector when in the held position and during a saliva ejection procedure and at least one projection configured to push tissue out of the way.

16. The saliva ejector system of claim 14 wherein the front face has at least one clamp in which the saliva ejector is positioned when in the held position.

17. The saliva ejector system of claim 14 wherein the elongate member includes an internal longitudinal wire configured to hold the elongate member in the desired changed shape.

* * * * *